(12) United States Patent
Gottschalk et al.

(10) Patent No.: US 9,480,862 B2
(45) Date of Patent: Nov. 1, 2016

(54) WATER EQUIVALENT DEPTH MEASUREMENT FOR PROVIDING A CONTINUOUS CALIBRATION RANGE BASED ON DISCRETE MEASUREMENTS

(75) Inventors: Bernard Gottschalk, Cambridge, MA (US); Yves Jongen, Louvain-la-Neuve (BE)

(73) Assignee: ION BEAM APPLICATIONS S.A., Louvain-La-Nueve (BE)

( * ) Notice: Subject to any disclaimer, the term of this patent is extended or adjusted under 35 U.S.C. 154(b) by 0 days.

(21) Appl. No.: 13/412,734

(22) Filed: Mar. 6, 2012

(65) Prior Publication Data
US 2012/0228493 A1 Sep. 13, 2012

Related U.S. Application Data

(60) Provisional application No. 61/449,785, filed on Mar. 7, 2011.

(51) Int. Cl.
*A61N 5/10* (2006.01)
*A61N 5/00* (2006.01)

(52) U.S. Cl.
CPC ............. *A61N 5/1075* (2013.01); *A61N 5/103* (2013.01); *A61N 2005/1087* (2013.01)

(58) Field of Classification Search
USPC ......................................................... 250/307
See application file for complete search history.

(56) References Cited

U.S. PATENT DOCUMENTS

| | | | | |
|---|---|---|---|---|
| 4,259,570 A * | 3/1981 | Leonard | ...................... | 250/214 A |
| 4,788,439 A * | 11/1988 | Hardy et al. | ............. | 250/559.38 |
| 5,489,780 A * | 2/1996 | Diamondis | .............. | 250/370.02 |
| 5,511,549 A * | 4/1996 | Legg et al. | ................... | 600/436 |
| 5,638,163 A * | 6/1997 | Nourrcier, Jr. | ............... | 356/5.01 |
| 5,748,802 A * | 5/1998 | Winkelman | ................... | 382/271 |
| 6,029,079 A * | 2/2000 | Cox et al. | ..................... | 600/407 |
| 6,133,989 A * | 10/2000 | Stettner et al. | ............. | 356/4.01 |
| 6,249,594 B1 * | 6/2001 | Hibbard | ....................... | 382/128 |
| 6,430,522 B1 * | 8/2002 | O'Brien et al. | .............. | 702/181 |
| 7,838,852 B2 * | 11/2010 | Rietzel | ....................... | 250/492.3 |
| 2003/0013978 A1 * | 1/2003 | Schlegel et al. | ............. | 600/509 |
| 2003/0065260 A1 * | 4/2003 | Cheng et al. | ................. | 600/427 |

(Continued)

OTHER PUBLICATIONS

A potential method for in vivo range verification in proton therapy treatment Hsiao-Ming Lu Phys. Med. Biol. 53 (2008) 1413-1424 Published Feb. 19, 2008 Online at stacks.iop.org/PMB/53/1413.*

*Primary Examiner* — Nicole Ippolito
*Assistant Examiner* — Sean Luck
(74) *Attorney, Agent, or Firm* — Finnegan, Henderson, Farabow, Garrett & Dunner LLP

(57) ABSTRACT

A method for determining a water equivalent depth between an entrance point and a reference point is disclosed. The method may comprise sending to a charged particle beam detector placed at a reference point within or beyond a body a charged particle beam whose energy is modulated between a minimum and maximum energy value, acquiring the time dependent response of said charged particle beam detector, determining from said time dependent response a value of a statistical parameter, providing a calibration curve expressing a relationship between values of said statistical parameter and water equivalent depths, and extracting from this calibration curve the water equivalent depth corresponding to the value of the statistical parameter determined from the time dependent response of the charged particle beam detector placed at the reference point.

24 Claims, 8 Drawing Sheets

(56) References Cited

U.S. PATENT DOCUMENTS

| | | | |
|---|---|---|---|
| 2003/0065482 A1* | 4/2003 | Bechhoefer | 702/183 |
| 2003/0220767 A1* | 11/2003 | Wegerich | 702/182 |
| 2004/0001633 A1* | 1/2004 | Caviedes | 382/228 |
| 2004/0061060 A1* | 4/2004 | Layman et al. | 250/370.02 |
| 2004/0162457 A1* | 8/2004 | Maggiore et al. | 600/1 |
| 2004/0164254 A1* | 8/2004 | Beloussov et al. | 250/492.1 |
| 2007/0043286 A1* | 2/2007 | Lu et al. | 600/407 |
| 2008/0217561 A1* | 9/2008 | Mackie et al. | 250/492.3 |

* cited by examiner

WATER EQUIVALENT DEPTH MEASUREMENT FOR PROVIDING A CONTINUOUS CALIBRATION RANGE BASED ON DISCRETE MEASUREMENTS

CROSS-REFERENCE TO RELATED APPLICATION

This application claims the benefit of priority under 35 U.S.C. §119 to U.S. Provisional Patent Application No. 61/449,785, filed on Mar. 7, 2011, which is incorporated herein by reference in its entirety.

FIELD OF THE DISCLOSURE

Embodiments of the present disclosure may relate to the field of charged particle therapy. More specifically, the present disclosure may relate to methods for determining a water equivalent depth between an entrance point and a reference point, said entrance point lying on an external surface of a body, said reference point being a point at which a charged particle beam detector is placed.

BACKGROUND OF THE DISCLOSURE

A property of charged particle therapy, such as proton therapy, includes the sharp fall-off of the dose-to-depth distribution induced by a charged particle beam traversing a body. This distribution is, however, sensitive to variations of the water equivalent depth ("WED") in tissues along a beam direction of the charged particle beam. This leads to uncertainties in treatment planning. Thus, a direct verification of the WED of a charged particle beam in a body is desirable.

In Lu, Hsiao-Ming, *A Potential Method for In Vivo Range Verification in Proton Therapy Treatment*, Phys. Med. Biol. 53, pp. 1413-1424 (2008) (the "Lu publication"), the time dependent response of a charged particle beam detector, such as an ionization chamber exposed to a time-dependent energy modulated proton beam, was studied as a function of the depth of the charged particle beam detector in a water tank.

To produce a time-dependent energy modulated proton beam, a modulator wheel as disclosed in the Lu publication may be employed. Such a wheel typically contains different segments of absorbing materials with various thicknesses. As the modulator wheel rotates, typically at a constant speed of 600 rotations per minute, the charged particle beam passes through one segment at a time. As a consequence, a charged particle beam that is time modulated between a minimum and maximum energy value is induced at the exit of the modulator wheel.

From the results of the survey published in the Lu publication, it was shown that a charged particle beam detector exposed to a charged particle beam that is time modulated in energy presents time dependent patterns that are characteristic of the depth at which the charged particle beam detector is placed in a water tank. So, these patterns may be employed as a unique coding of the WEDs. The collection of the patterns at different depths of the charged particle beam detector may be viewed as forming a ruler, where each mark corresponds to a unique pattern. This ruler may be obtained during a calibration phase by measurement or by calculation of the time dependent response of a charged particle beam detector that is placed (or assumed to be placed) at different depths in a phantom, such as a water tank. Afterwards, by positioning the charged particle beam detector used in the calibration phase at a reference point (e.g., a target in a body), the WED corresponding to this reference point may be deduced by matching the pattern measured by the charged particle beam detector at the reference point to one of the patterns determined in the calibration phase.

The Lu publication proposes a method for this pattern matching that is minimizing the following least-square difference $$L(x) = \int_0^T [\lambda f_m(t) - f_r(x,t)]^2 dt \qquad \text{(Eq. 1)}$$

with respect to depth x. The depth x corresponding to the minimum value of L(x) is the sought WED. The function $f_r(x,t)$ represents the patterns determined during the calibration phase, and $f_m(t)$ is the measured time dependent response of the charged particle beam detector positioned at the WED to be determined. The function L(x) is also minimized with respect to a scale factor $\lambda$ because the pattern matching has to be purely based on the shape of the time dependence of the measured signal, independently of its absolute magnitude.

By using the method proposed in the Lu publication, one can hope to have a WED precision of about 1 mm in a homogeneous water phantom. A drawback of the method proposed by the Lu publication is the necessity to measure enough patterns at enough different depths during the calibration phase when a fine WED resolution is wanted. This leads to a relatively long calibration phase when such a fine WED resolution is desired.

SUMMARY OF THE DISCLOSURE

In accordance with an embodiment, a method for determining a water equivalent depth between an entrance point and a reference point, said entrance point lying on an external surface of a body, said reference point being a point at which a charged particle beam detector is placed, may include providing an apparatus for delivering a charged particle beam to said body in a beam direction defined from said entrance point to said reference point, choosing a maximum energy value such that a charged particle beam having said maximum energy value and being sent in said beam direction penetrates the body from said entrance point up to at least said reference point, choosing a minimum energy value such that a charged particle beam having said minimum energy value and being sent in said beam direction penetrates the body from said entrance point and is stopped in said body before reaching said reference point, sending in said beam direction a charged particle beam that is time modulated in energy between said minimum energy value and said maximum energy value, acquiring a time dependent response of the charged particle beam detector, determining a value of a statistical parameter of said time dependent response, providing a pre-determined calibration curve expressing a relationship between values of said statistical parameter and water equivalent depths, and determining from said calibration curve the water equivalent depth between the entrance point and the reference point corresponding to the value of the determined statistical parameter.

In accordance with another embodiment, a device for determining a water equivalent depth between an entrance point and a reference point, said entrance point lying on an external surface of a body, may include a charged particle beam detector that is placed at the reference point, a subunit for acquiring a time dependent response of said charged particle beam detector, a subunit for determining a value of a statistical parameter of said time dependent response, a subunit for loading a pre-determined calibration curve expressing a relationship between values of said statistical parameter and water equivalent depths, and a subunit for determining from said calibration curve the water equivalent depth corresponding to the value of the statistical parameter of the time dependent response of the charged particle beam detector placed at the reference point.

In yet another embodiment, a method for determining a water equivalent depth between a number of entrance points and a number of corresponding reference points, said entrance points being located on an external surface of a body, said corresponding reference points being points where a corresponding charged particle beam detector is placed, may comprise, for each entrance point and corresponding reference point, may include providing an apparatus for delivering a charged particle beam to said body in a beam direction defined from an entrance point to the correspond reference point, choosing a maximum energy value such that a charged particle beam having said maximum energy value and being sent in said beam direction penetrates the body from said entrance point up to at least said reference point, choosing a minimum energy value such that a charged particle beam having said minimum energy value and being sent in said beam direction penetrates the body from said entrance point and is stopped in said body before reaching said reference point, sending in said beam direction a charged particle beam that is time modulated in energy between said minimum energy value and said maximum energy value, acquiring a time dependent response of the charged particle beam detector, wherein, for each time dependent response curve obtained for each of the said corresponding detectors, further comprising the steps of determining a value of a statistical parameter of the time dependent response, providing a pre-determined calibration curve expressing a relationship between values of said statistical parameter and water equivalent depths, and determining from said calibration curve the water equivalent depth between the entrance point and the reference point corresponding to the determined value of the statistical parameter.

In yet another embodiment, a method for determining range mixing when a water equivalent depth between a number of entrance points and a number of corresponding reference points is being measured using a charged particle beam, said entrance points being located on an external surface of a body, said corresponding reference points being points where a corresponding charged particle beam detector is placed, may comprise, for each entrance point and corresponding reference point, providing an apparatus for delivering a charged particle beam to said body in a beam direction defined from an entrance point to the correspond reference point, choosing a maximum energy value such that a charged particle beam having said maximum energy value and being sent in said beam direction penetrates the body from said entrance point up to at least said reference point, choosing a minimum energy value such that a charged particle beam having said minimum energy value and being sent in said beam direction penetrates the body from said entrance point and is stopped in said body before reaching said reference point, sending in said beam direction a charged particle beam that is time modulated in energy between said minimum energy value and said maximum energy value, acquiring a time dependent response of the charged particle beam detector, wherein, for each time dependent response curve obtained for each of the said corresponding detectors, further comprising the steps of determining statistical probabilities of skewness and/or kurtosis with respect to the time dependent response curve, comparing statistical probabilities of skewness and/or kurtosis obtained in the previous step with values obtained during a calibration measurement using a water phantom, computing a range mixing parameter which is an indicator of the observed deviations in probabilities of skewness and/or kurtosis, and classifying the beam detectors according to the range mixing parameter.

In yet another embodiment, a device configured to determine a water equivalent depth between an entrance point and a reference point, said entrance point lying on an external surface of a body, said reference point being a point at which a charged particle beam detector is placed, may comprise a first software module configured to acquire a time dependent response of said charged particle beam detector, a second software module configured to determine a value of a statistical parameter of said time dependent response, a third software module configured to load a pre-determined calibration curve expressing a relationship between values of said statistical parameter and water equivalent depths, and a fourth software module configured to determine from said calibration curve the water equivalent depth corresponding to the value of the statistical parameter of the time dependent response of the charged particle beam detector placed at the reference point.

The present disclosure may be directed to a method for determining the WED of a charged particle beam that requires a shorter calibration procedure.

According to the present disclosure, different statistical parameters of time dependent responses of charged particle beam detectors when such detectors may be subjected to a charged particle beam that is time modulated in energy have been evaluated. More precisely, the variation of such values when the charged particle beam detectors may be positioned at different depths in a water tank have been evaluated. Such values may be smoothly and monotonically dependent on the depths of the charged particle beam detectors in the water tank. Thanks to this smooth dependence, a curve may be found by, for example, interpolation, that relates these values to the different depths. By identifying these different depths to WEDs, a calibration curve relating values of one or of different statistical parameters to WEDs may be produced. Because of the smooth variation of the values of certain statistical parameters to the different depths, only a few points may need to be determined in a calibration procedure. As a consequence, the methods of the present disclosure may require a shorter calibration phase than conventional methods. Once having this calibration curve, the WED of a reference distance pointing to a position where a charged particle beam detector is placed may be determined.

The present disclosure may also be directed to a method for determining the WED of a charged particle beam with a higher precision. To this end, such a method may be characterized in that a statistical parameter may be a root mean square width of a time dependent response. The method of the present disclosure may use a value of a root mean square width for determining the WED, which may present a higher accuracy. As will be discussed below, a precision of around 0.3 mm in WED determination may be obtained, which is more accurate than the precision of around, for example, 1 mm in conventional methods.

The present disclosure may further be directed to a method for determining the WED as a direct verification during or just before the actual treatment, for example, in cases where the dose rate function may be measured with a detector in a body cavity (e.g., the oral cavity, the esophagus, or the rectum). To this end, the method of the present disclosure may be characterized in that a reference point is positioned inside the body into which the particle beam travels. As the charged particle beam detector is positioned at the reference point, the charged particle beam may then consist in an implantable charged particle beam detector.

Additionally, the present disclosure may be directed to a method that does not need any insertion of a charged particle beam detector in a body for the determination of the WED of a charged particle beam traversing said body. To this end, the method of the present disclosure may be characterized in that the reference point may be positioned outside the body through which the charged particle beam travels. As the charged particle beam detector is positioned at the reference point, the charged particle beam detector may not need to be inserted into the body. The detector may be, for example, directly fixed to the patient or attached to a patient table.

The present disclosure may also be directed to a method that uses a small, rugged, and inexpensive charged particle beam detector. To this end, the charged particle beam detector may comprise a semiconductor diode for detecting the charged particle beam. Semiconductor diodes may be suitable charged particle beam detectors that may be small, rugged, and inexpensive.

The present disclosure may be directed to a method to obtain a pre-determined calibration curve experimentally.

Furthermore, the present disclosure may be directed to a method that allows a study of the spatial variation of the WED in a body. To this end, the method of the present disclosure may be characterized in that the charged particle beam detector may comprise an array of semiconductor diodes placed transversally with respect to the charged particle beam. By acquiring the time dependent responses of each semiconductor diode of the array, a value of a statistical parameter for each position of such diodes may be deduced and the corresponding WEDs may be determined. By comparing these WEDs, the spatial variation of the WED in a body may be evaluated.

The present disclosure may also be directed to a device for determining a WED between an entrance point and a reference point, said entrance point lying on an external surface of a body.

The present disclosure may further be directed to a program for determining the WED between an entrance point and a reference point, said entrance point lying on an external surface of a body, said reference point being a point at which a charged particle beam detector is placed.

When determining a WED using a charged particle beam, a problem of so-called range mixing may occur, and when using a number of beam detectors (e.g., array of diodes), each beam detector may observe a different amount of range mixing. Therefore, the present disclosure may further be directed to a method for determining a range mixing parameter which is based on a comparison of the skewness and/or kurtosis of the time dependent response and/or the skewness and kurtosis obtained when using a water phantom.

In this respect, before explaining multiple embodiments of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

DETAILED DESCRIPTION

Figure 1:
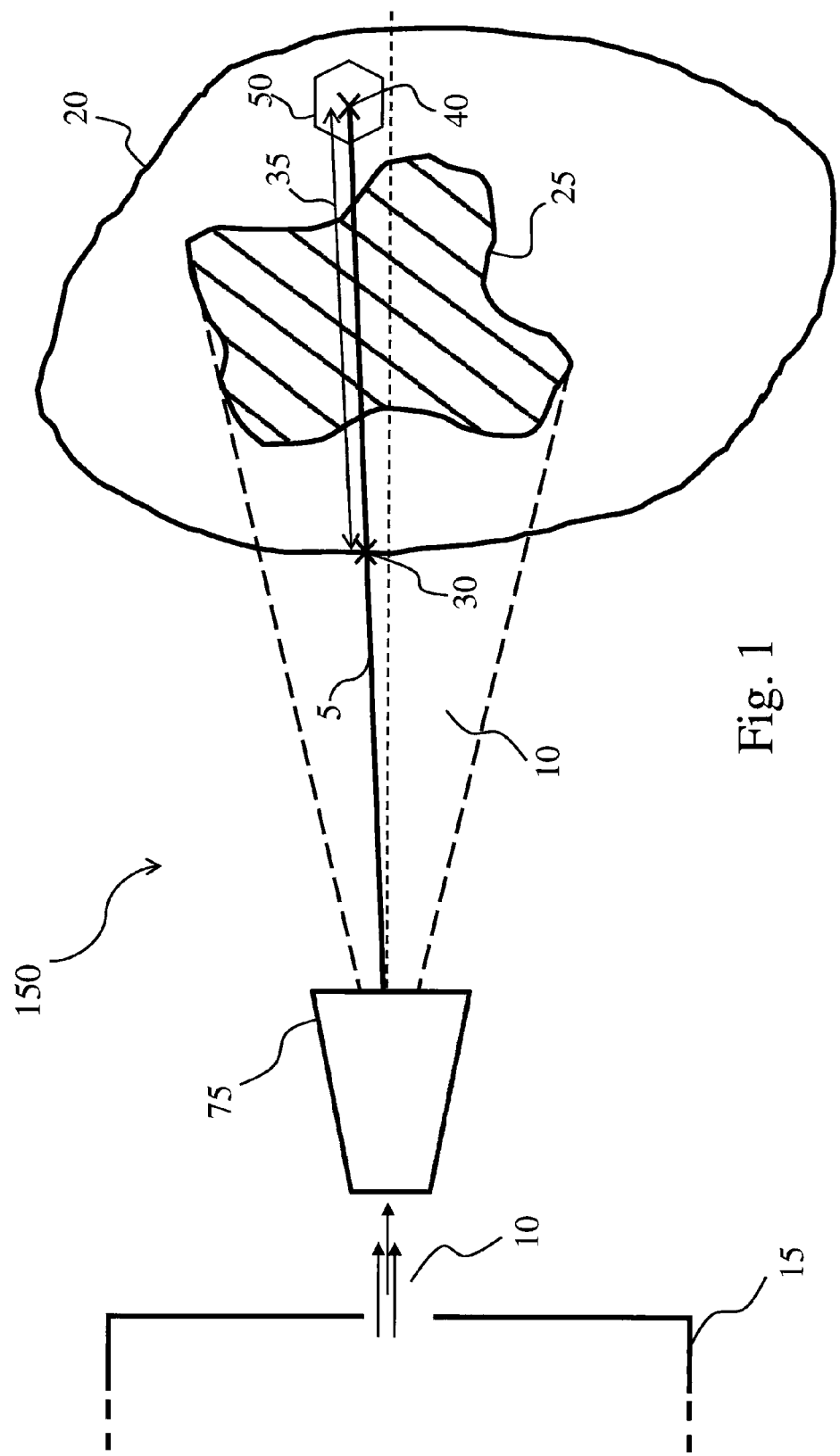
FIG. 1 illustrates a measurement setup, according to an exemplary disclosed embodiment.
Figure 4:
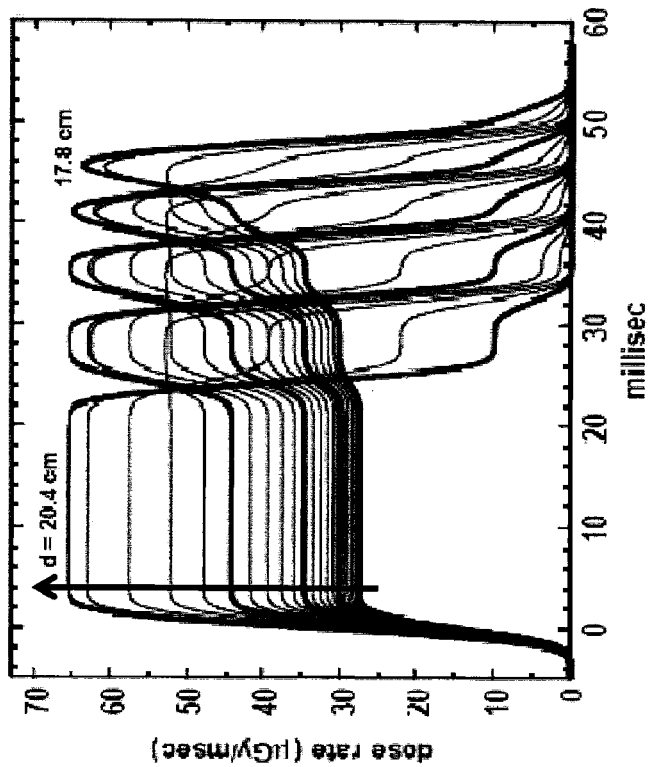
FIG. 4 illustrates time dependent dose rates calculated at twenty-one different depths in a water tank along a beam direction of a charged particle beam that is time modulated in energy, according to an exemplary disclosed embodiment.
Figure 12:
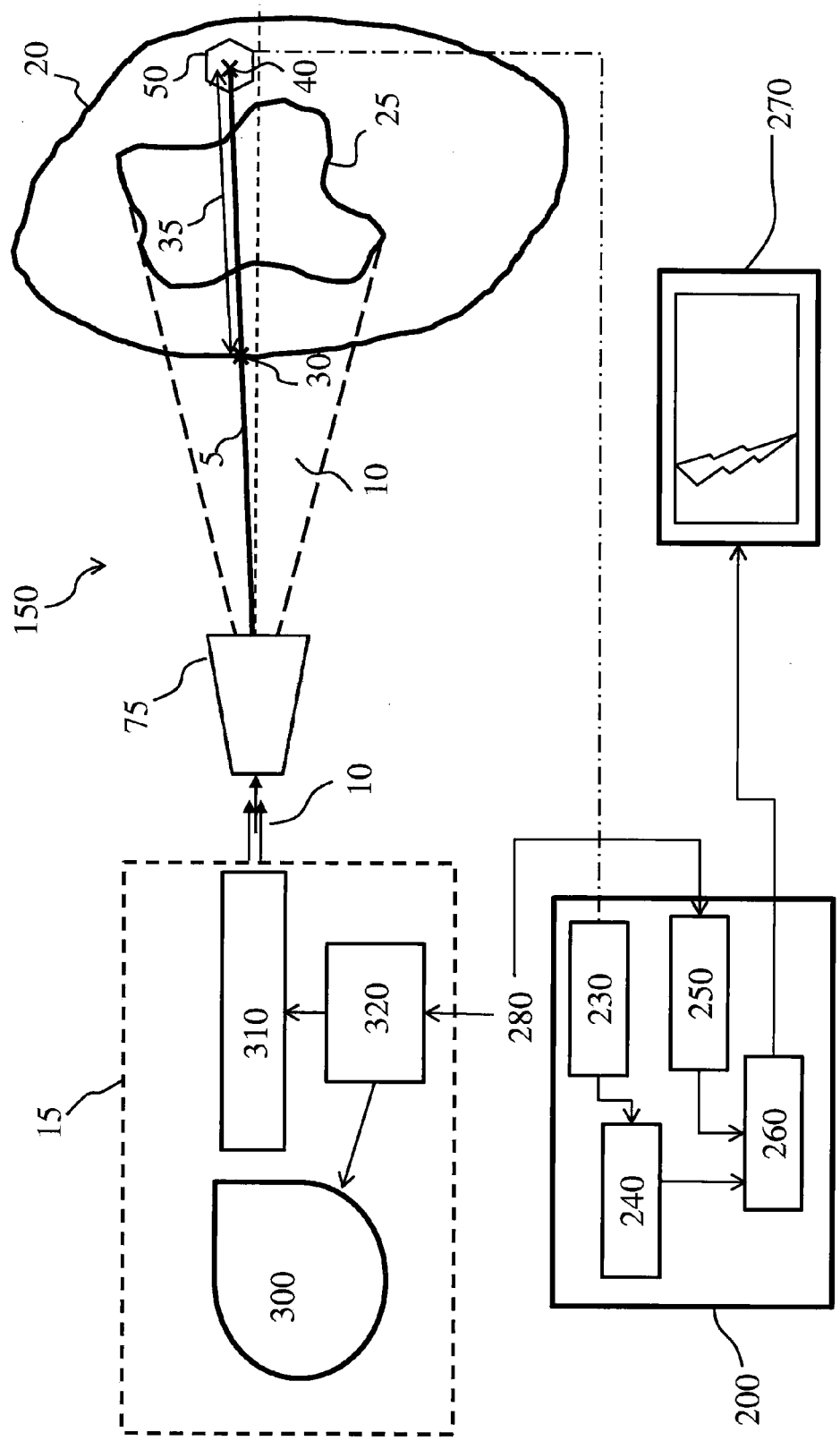
FIG. 12 illustrates a device, according to an exemplary disclosed embodiment.

FIG. 1 illustrates an exemplary setup 150 that may be used for charged particle therapy. Charged particle therapy may include sending to a target volume 25 a charged particle beam 10. Setup 150 may include a suitable apparatus 15 configured to send charged particle beam 10, such as a proton beam, to a body 20 having target volume 25 to be irradiated for treatment. It should be appreciated that target volume 25 may be generally much smaller than body 20. Similarly, apparatus 15 may be typically much larger than body 20. As shown in FIG. 12, apparatus 15 may typically include an accelerator 300 of charged particles, such as a cyclotron, a beamline 310 configured to transport charged particle beam 10 to body 20, and a control system 320 configured to control accelerator 300 and beamline 310. To irradiate the entire target volume 25, charged particle beam 10 may be scattered via a nozzle 75, as shown in FIG. 1. As a result of the scattering process, charged particle beam 10 at the exit of the nozzle 75 may be wide and diverging. To irradiate the entire target volume 25 in certain other embodiments, a magnetically scanned beam may be employed (typically, the scanning process may take place in nozzle 75 by use of scanning magnets). In this case, the charged particle beam 10 penetrating the body 20 may be more concentrated (and sometimes named pencil beam) but may be typically scanned by using varying magnetic fields that may change a beam direction 5 of charged particle beam 10. The scanning process may allow the entire target volume 25 to be irradiated.

Figure 2:
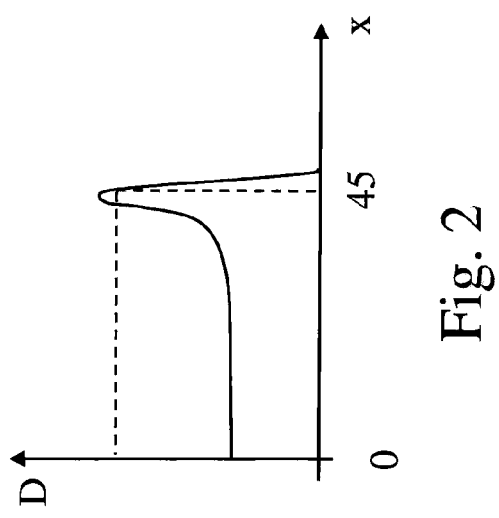
FIG. 2 illustrates a Bragg peak, according to an exemplary disclosed embodiment.

If one considers charged particle beam 10 having a given energy, the variation of the dose that may be induced in body 20 at different depths along beam direction 5 may have an exemplary shape as illustrated in FIG. 2. FIG. 2 shows an exemplary illustration of a Bragg peak (D stands for the dose, and x for the depth in body 20). The zero value of the depth x may correspond to the entry of charged particle beam 10 in body 20. A depth 45 may be defined as up to which charged particle beam 10 penetrates. Beyond this depth 45, charged particle beam 10 may be stopped. This depth 45 may be generally defined as the depth before which the dose falls below a given threshold after the peak, for example, 90% of the maximum dose induced in the body, which means 90% of the dose value corresponding to the maximum of the Bragg peak. It should be appreciated that any percentage other than 90% may be chosen.

Figure 3:
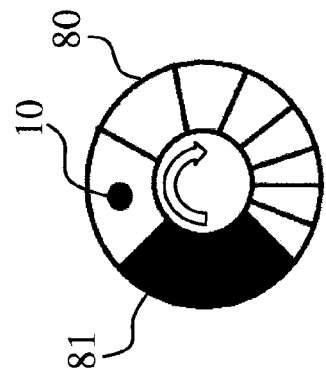
FIG. 3 illustrates a modulator wheel, according to an exemplary disclosed embodiment.

In order to irradiate target volume 25 along its entire depth, charged particle beam 10 that presents different energy values may be employed. This may lead to different depths 45 up to charged particle beam 10 penetrates and so to different depths at which a maximum dose may be delivered. One possibility to have charged particle beam 10 that is modulated in energy may be to send it through an energy modulator, for instance, through a modulator wheel 80. When a scattered beam is used, such a modulator wheel 80 may be inserted in the nozzle before scattering takes place. FIG. 3 shows an exemplary illustration of modulator wheel 80. Modulator wheel 80 may comprise a series of segments that have absorbing materials of different thicknesses. Black segment 81 of modulator wheel 80 show in FIG. 2 may correspond to a total absorption of an incident charged particle beam 10. Modulator wheel 80 may be configured to spin at a constant speed, for instance, 600 rotations per minute. The black point in FIG. 2 shows the place where charged particle beam 10 crosses modulator wheel 80 for a given angular position of the modulator wheel 80. As modulator wheel 80 rotates, charged particle beam 10 that points towards a given position may pass through different segments having different absorbing properties. As a consequence, charged particle beam 10 may induce in body 20 a series of Bragg peaks spread out in depth. By properly specifying the angular span of each segment of the range modulator, the superposition of these Bragg peaks may form a flat region in the depth-dose distribution, i.e., a region having an uniform dose, which is commonly referred to as a spread-out Bragg peak (SOBP).

A method of the present disclosure aims at determining a water equivalent depth 1 between an entrance point 30 and a reference point 40. Entrance point 30 may lie on an external surface of body 20. Two examples for body 20 may be a phantom and a human body. Beam direction 5 may be defined from entrance point 30 to reference point 40. Accordingly, reference point 40 may lie downstream entrance point 30 along such beam direction 5. FIG. 1 illustrates an example of entrance point 30 and reference point 40. Reference point 40 may lie preferably inside body 20, but reference point 40 may also be located on an external surface of body 20 or outside of body 20. When reference point 40 is inside body 20, it may be located in a natural cavity, such as the rectum, or under the skin of body 20. A charged particle beam detector 50 may be placed at reference point 40. Two examples of charged particle beam detector 50 may include an ionization chamber and a semiconductor diode 110.

The method may be carried out by setup 150 or apparatus 15. More particularly, the method may be employed with a system having a scattering or a scanning nozzle 75. In the latter case, the magnetic settings of the scanning magnets may be set such that a pencil charged particle beam 10 points along the beam direction 5 discussed above.

The method further includes choosing a maximum 65 and minimum 70 energy value. Maximum energy value 65 may be such that charged particle beam 10 having this maximum energy value 65 and being sent in beam direction 5 discussed above may penetrate body 20 from said entrance point 30 up to at least said reference point 40. Distance 45 up to charged particle beam 10 penetrates is discussed above in FIG. 2. Minimum energy value 70 may be such that charged particle beam 10 having this minimum energy value 70 and being sent in beam direction 5 defined above may penetrate body 20 from said entrance point 30 and may be stopped in body 20 before reaching reference point 40. Distance 45 up to which charged particle beam 10 may penetrate in a body 20 is discussed above in FIG. 2. Such energy values may be obtained from a treatment planning if at least approximately the absorption properties of body 20 along beam direction 5 is known.

The method of the present disclosure further includes sending in beam direction 5 charged particle beam 10 that may be time modulated in energy between minimum 70 and maximum 65 energy values defined above. This means that the energy of charged particle beam 10 may vary in time between minimum 70 and maximum 65 energy values. Preferably, the time variation of the energy of charged particle beam 10 may be a monotically decreasing function from maximum 65 to minimum 70 energy values. More preferably, the time variation of the energy of charged particle beam 10 may be a periodic function with respect to time. To modulate the energy of charged particle beam 10, modulator wheel 80 may be utilized, as defined above in FIG. 2. Typically, such a modulator wheel 80 may rotate with a period equal to modulator cycle 85. A typical value of modulator cycle 85 may be 100 ms. So, by using apparatus 15, nozzle 75, and an energy modulator, one may send in beam direction 5 a charged particle beam 10 that may be time modulated in energy between minimum 70 and maximum 65 energy values. A range modulator may be preferably designed for providing a flat SOBP, and minimum 70 and maximum 65 energy values may be preferably chosen such that the WED to be measured (i.e., reference point 40) falls in the flat SOBP region. Other types of range modulators which do not provide a flat SOBP (for example, tilted SOBP) may also be employed.

Charged particle beam 10 that is time modulated in energy may induce in body 20 a time dependent dose rate 60. When modulator wheel 80 is used, induced time dependent dose rate 60 may be periodic in time with a period equal to modulator cycle 85. At different positions lying in body 20 and along beam direction 5 of charged particle beam 10 that is time modulated in energy, the shape of the corresponding time dependent dose rates 60 versus time may change. These different shapes may be the characteristic patterns 105 referred in the Lu publication. As a further illustration, FIG. 3 shows time dependent dose rates 60 calculated at twenty-one different depths along a beam direction of an energy modulated charged particle beam 10 when these twenty-one different depths correspond to depths in a water tank (the different curves correspond to increasing depths along the vertical arrow of FIG. 3). Different characteristic patterns at the different depths may be observed.

As charged particle beam 10 that is time modulated in energy between minimum energy value 70 and maximum energy value 65 is delivered, time dependent dose rate 60 is induced along a beam direction 5 of this charged particle beam 10. If minimum 70 and maximum 65 energy values are chosen as explained above, charged particle beam detector 50 placed at reference point 40 may present a time dependent response 55 that may include stepwise structures spaced in time by modulator cycle 85 if modulator wheel 80 is used to produce the energy modulated charged particle beam 10. Similar to time dependent dose rate 60, time dependent responses 55 of charged particle beam detector 50 may present characteristic patterns when said charged particle beam detector 50 is placed at different positions along beam direction 5 of charged particle beam 10 that is time modulated in energy. The method of the present disclosure may further include acquiring time dependent response 55 of charged particle beam detector 50. The way to obtain time dependent response 55 of charged particle beam detector 50 by any suitable method, such as, for example, that described in the Lu publication, which incorporated herein by reference in its entirety.

The WED corresponding to distance 35 between entrance point 30 and reference point 40 may be related to a value of a statistical parameter 100 of time dependent response 55 of charged particle beam detector 50, when charged particle beam detector 50 is subjected to charged particle beam 10 that is time modulated in energy. Different statistical parameters 100 may be chosen for determining the sought WED. An example is the skewness sk, which is described below.

From time dependent response 55 of charged particle beam detector 50, the following parameters may be defined. The sum, S, is given by:

$$S = \sum_{i=i_1}^{i_N} v_i \quad \text{(Eq. 2)}$$

when time dependent response 55 is a discrete signal and by:

$$S = \int_{t_1}^{t_N} v(t) dt \quad \text{(Eq. 3)}$$

when time dependent response 55 is a continuous signal. In these equations, v stands for time dependent response 55 of charged particle beam detector 50. In Eq. 2, the index $i_1$ (resp. $i_N$) is the index of the first (resp. last) reading of time dependent response 55. When time dependent response 55 is continuous, $t_1$ (resp. $t_N$) is the time of the beginning (resp. end) of its acquisition.

The mean time of occurrence, m, of time dependent response 55 is defined by:

$$m = \frac{1}{s} \sum_{i_1}^{i_N} v_i t_i \quad \text{(Eq. 4)}$$

when time dependent response 55 is a discrete signal and by:

$$m = \frac{1}{s} \int_{t_1}^{t_N} v(t) t \, dt \quad \text{(Eq. 5)}$$

when time dependent response 55 is a continuous function, S being given by Eq. 2 (discrete case) or Eq. 3 (continuous case). The root mean square width 101, σ, is given by:

$$\sigma = \sqrt{\frac{1}{s} \sum_{i_1}^{i_N} v_i (t_i - m)^2} \quad \text{(Eq. 6)}$$

when time dependent response 55 is a discrete signal and by:

$$\sigma = \sqrt{\frac{1}{s} \int_{t_1}^{t_N} v(t)(t - m)^2} \quad \text{(Eq. 7)}$$

when time dependent response 55 is a continuous function. The skewness if given by:

$$sk = \frac{1}{s\sigma^3} \sum_{i_1}^{i_N} v_i (t_i - m)^3 \quad \text{(Eq. 8)}$$

in the discrete case, and by:

$$sk = \frac{1}{s\sigma^3} \int_{t_1}^{t_N} v(t)(t - m)^3. \quad \text{(Eq. 9)}$$

The parameters S and m entering Eq. 6 to Eq. 9 are given by Eq. 2 and Eq. 4 in the discrete case and by Eq. 3 and Eq. 5 in the continuous case.

Figure 5:
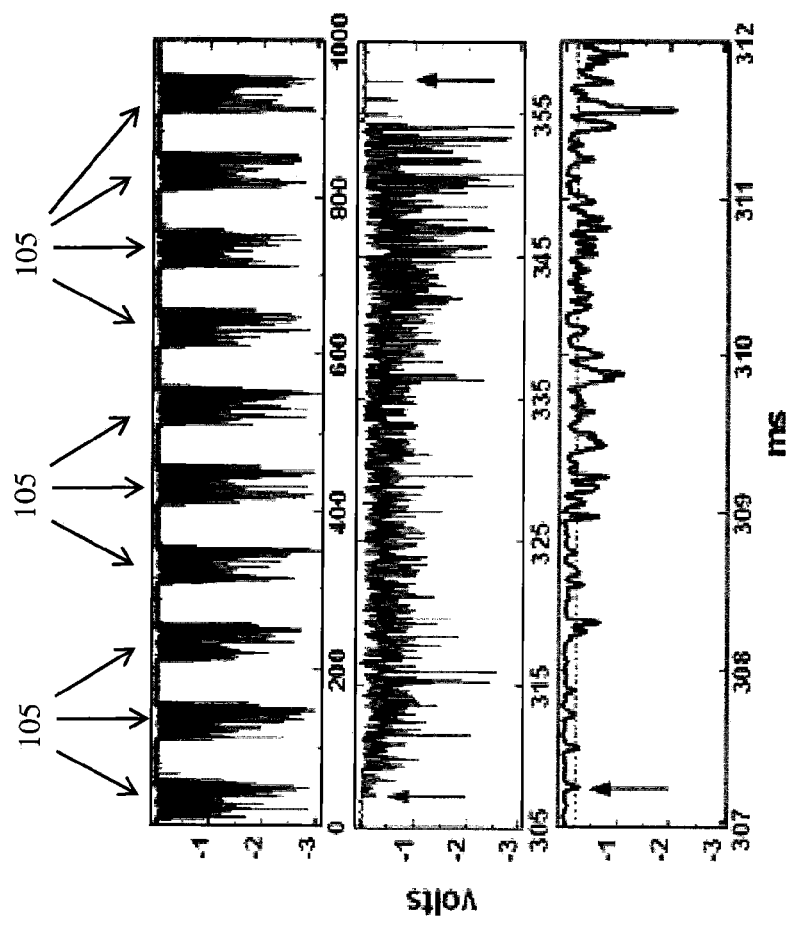
FIG. 5 illustrates time dependent response of a PTW Model T60012 semiconductor diode that is placed in a water phantom and subjected to a charged particle beam that is time modulated in energy, according to an exemplary disclosed embodiment.

When modulator wheel 80 is used, time dependent response 55 of charged particle beam detector 50 may present periodic patterns 105 separated in time by a period equal to modulator cycle 85 as shown in FIG. 5 (top graph). Rather than acquiring the whole signal of time dependent response 55 of charged particle beam detector 50 before determining the value of a statistical parameter 100 such as the skewness, its response may be recorded during only one of its periods by the use of synchronizing means. Then, Eq. 8 or Eq. 9 may be applied to determine the value of the skewness corresponding to said period. To increase statistics and precision, the measurement of the time dependent response may also be performed over multiple cycles of the range modulator.

As time dependent response 55 of charged particle beam detector 50 subjected to an energy modulated charged particle beam 10 may present a stepwise structure, the different steps may also be isolated from the background measured level before applying Eq. 8 or Eq. 9 when time dependent response 55 is acquired during a time longer than modulator cycle 85. Values of a statistical parameter 100 corresponding to different periods of the time dependent response 55 may also be calculated, and after, averaging these values over the different periods to obtain an average value of the chosen statistical parameter 100. This procedure may be useful when time dependent response 55 has a low signal to noise level. Alternatively, the data acquisition system may operate in synchrony with the rotation of range modulator wheel 80 so as to obtain an accumulated time dependent response signal.

FIG. 5 illustrates time dependent response 55 of a charged particle beam detector 50 that is a PTW Model T60012 semiconductor diode when such a diode is placed at a given depth (e.g., 16.5 cm) in a water phantom and subjected to a charged particle beam 10 that is time modulated in energy. In this example, time dependent response 55 of charged particle beam detector 50 is a time dependent negative voltage. The upper part of FIG. 5 shows ten patterns corresponding to ten modulator cycles 85 of modulator wheel 80 that may be used for producing the energy modulated charged particle beam. Modulator cycle 85 may be equal to 100 ms in this example. The middle graph of FIG. 5 is a zoom of the fourth cycle, whereas the lower graph shows only the beginning of the same fourth cycle. The used diode may present a disk of area 1 mm$^2$ and a thickness equal to 2.5 μm (2.5 μm may be the thickness of charged particle beam detector 50 along beam direction 5 of charged particle beam 10). The diode may be connected to a transimpedance amplifier 120 whose details are given below.

When a signal such as the one depicted in FIG. 5 is acquired, the different patterns 105 or real signals may first be isolated from the background level. As an example, the first pattern 105 may be deemed to begin when a voltage reading is more negative than a given discrimination level. After, one may take advantage of the stable mean time between each pattern 105 that is typically equal to modulator cycle 85 to remove occasional spurious pulses between each pattern. Knowing the value of modulator cycle 85, one does not need to seek the second pattern 105 until, for example, 98 ms after the first one if modulator cycle 85 is equal to 100 ms. Continuing thus, one may identify all the ten patterns 105 of FIG. 5 and determine for each of them the value of a statistical parameter 100, such as the skewness. In this case, the index $i_1$ (resp. $i_N$) entering Eq. 2, Eq. 4, Eq. 6, and Eq. 8 may be the index of the first (resp. last) reading of each pattern 105 isolated from the background level. Knowing the different values of a statistical parameter 100 corresponding to the different patterns, one may easily calculate an averaged value of such a statistical parameter 100. Preferably, one may acquire time dependent response 55 during a time that is longer than ten modular cycles 85 and determine more than ten values of a statistical parameter 100 before calculating an averaged value of such a statistical parameter 100.

Once time dependent response 55 of charged particle beam detector 50 that is positioned at different depths in a water tank and that is subjected to charged particle beam 10 that is time modulated in energy is acquired, each depth the value of a statistical parameter 100, such as the skewness, may be deduced by using Eq. 8 or Eq. 9. By following this procedure, such a statistical parameter 100 may be smoothly and monotonically related to the depth of charged particle beam detector 50 in the water tank. As a consequence, the dependence of said statistical parameter 100 to the depth of charged particle beam detector 50 in the water tank may be well represented by a curve, and such a curve may be used as a calibration curve 95. Indeed, the depths of charged particle beam detector 50 with respect to the entrance point of charged particle beam 10 in the water tank can be identified to WEDs. The method of the present disclosure aims at providing such a calibration curve 95. There may be different possibilities to obtain such a calibration curve 95. The time dependent response 55 of charged particle beam detector 50 that is positioned at different depths in a water tank and that is subjected to charged particle beam 10 that is time modulated in energy may be measured. Or, calibration curve 95 may be obtained from calculations that predict the time dependent response 55 of charged particle beam detector 50 placed at different depths in a water tank and exposed to an energy modulated charged particle beam 10. The conditions of the calibration procedure may be the same as those used during the acquisition of the time dependent response 55 of charged particle beam detector 50 placed at reference point 40. Instead of a calibration curve 95, a calibration table may be established.

Figure 6:
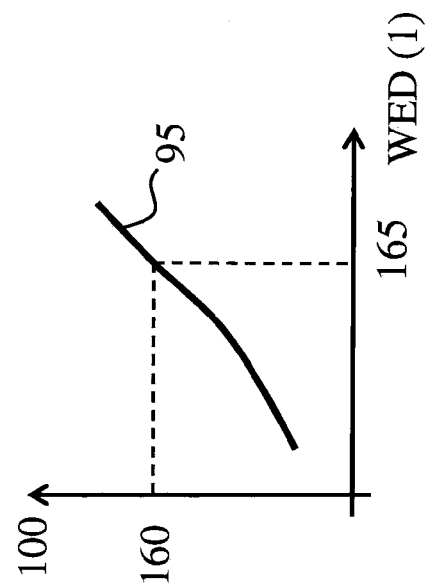
FIG. 6 illustrates a schematic calibration curve, according to an exemplary disclosed embodiment.

By using calibration curve 95 provided above, the WED corresponding to the value of the statistical parameter 100 may be determined. As an illustration and referring to FIG. 6, if the determined value of the statistical parameter 100 is equal to a value 160, the corresponding WED may be equal to a value 165.

Figure 8:
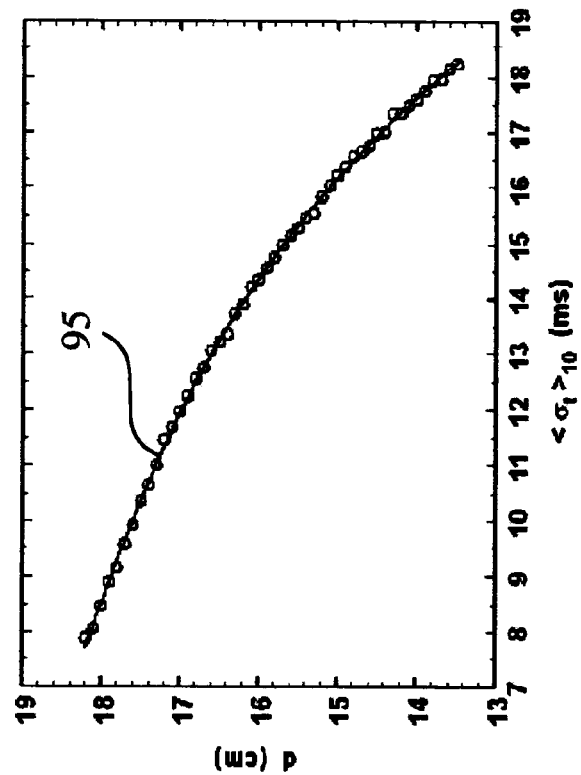
FIG. 8 illustrates another experimental calibration curve, according to an exemplary disclosed embodiment.
Figure 7:
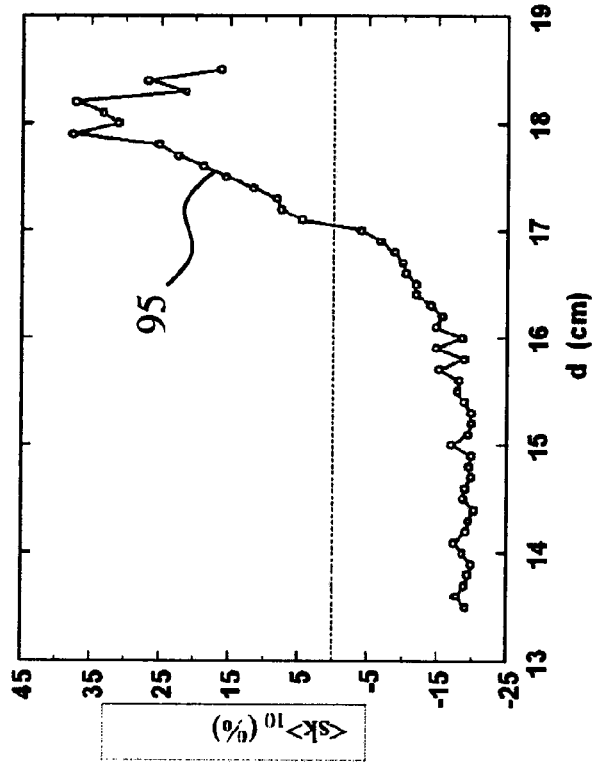
FIG. 7 illustrates an experimental calibration curve, according to an exemplary disclosed embodiment.

The statistical parameter 100 that may be used for determining the WED may be the root mean square width 101 of the time dependent response 55 of charged particle beam detector 50. The root mean square width 101 may be obtained from Eq. 2, Eq. 4, and Eq. 6 (discrete case), or Eq. 3, Eq. 5, and Eq. 7 (continuous case). When using such a statistical parameter 100, the region of good sensitivity may be large. This is illustrated in FIGS. 7 and 8, which show two measured calibration curves 95 corresponding to the variations of two different statistical parameters 100 with respect to the depth of charged particle beam detector 50 in a water tank. FIGS. 7 and 8 show a calibration curve 95 when the statistical parameter 100 is a skewness (respectively root mean square width 101). The region of good sensitivity may be narrower for the skewness as the slope of the curve of FIG. 7 is smaller than the slope of the curve of FIG. 8.

Figure 9:
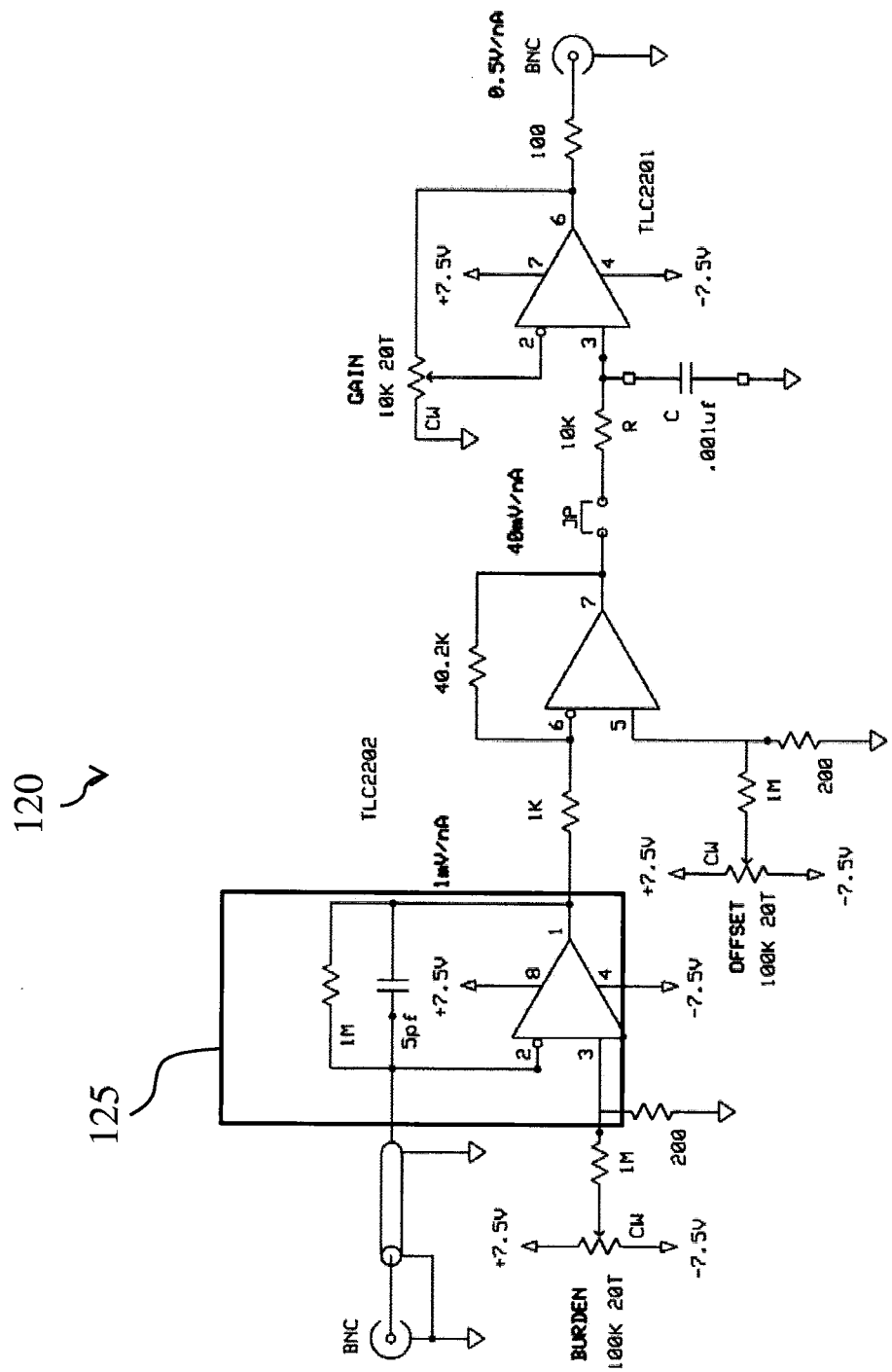
FIG. 9 illustrates a transimpedance amplifier, according to an exemplary disclosed embodiment.

Different charged particle beam detectors 50 may be used to carry out the method of the of the present disclosure. In one embodiment, charged particle beam detector 50 comprises a semiconductor diode 110. Ordinary semiconductor diodes 110 may make good charged particle beam detectors 50 and present some advantages: small, rugged, and inexpensive. In yet another embodiment, charged particle beam detector 50 comprises a PTW Model T60012 diode connected to a transimpedance amplifier 120. In yet another embodiment, transimpedance amplifier 120 may have three stages. The first stage may be a first transimpedance amplifier 125 with an output of 1 mV/nA and a response time of 5 μs dominated by the feedback circuit. The next stage may be an inverting voltage amplifier with a gain of 40. The output stage gain may be set for a total gain of 0.5 V/nA using a precise current source. Since it is very convenient for the quiescent DC offset to be zero and stable, regulated on-board tracking 7.5 V regulators may be provided. The amplifier may have two DC adjustments. 'OFFSET' may be set to null the output when the input is open. 'BURDEN' may be set to null the output when the input is grounded through preferably 10 kΩ. Such a transimpedance amplifier, which is illustrated in FIG. 9, may be connected to an oscilloscope through a coaxial cable.

Calibration curve 95 that may be used to link the value the statistical parameter 100 to the WED may be obtained experimentally. In one embodiment, such an experimental determination may comprise the following steps:
  i. positioning said charged particle beam detector 50 at a given position 170 in a water or water-equivalent calibration phantom 115;
  ii. sending to said charged particle beam detector 50 the charged particle beam 10 that may be time modulated in energy between said minimum 70 and said maximum 65 energy value;
  iii. acquiring a time dependent response 55 of said charged particle beam detector 50;
  iv. determining a value of said statistical parameter 100 from said time dependent response 55;

v. determining a water equivalent depth 1, said water equivalent depth 1 being the distance between the entrance point of said charged particle beam 10 in said calibration phantom 115 and said given position 170;

vi. repeating steps i. to v. n times, n being an integer larger than one; and vii. establishing a calibration curve 95 that relates the values of the statistical parameter 100 determined in step iv and the water equivalent depth 1 determined in step v.

When statistical parameter 100 is a root mean square width 101, the calibration curve 95 of step vii may be a cubic polynomial curve. Adding higher order terms may not improve the fit quality and the precision significantly.

In another embodiment, charged particle beam detector 50 may comprise an array of semiconductor diodes 110 placed transversally with respect to charged particle beam 10. The semiconductor diodes 110 may then spread over a few cm², for example, on a flex circuit attached to a rectal balloon. By using such an array, the value of a statistical parameter 100, preferably a root mean square width 101, may be deduced for each semiconductor diode 110 by using the method of the present disclosure. By comparing the different values corresponding to the different semiconductor diodes 110, the spatial variation of the WED in the body 20 may be evaluated or a mean value over the area covered by the array of semiconductor diodes 110 may be obtained.

When using, for example, a scattering system for producing a broad proton beam, such a beam may diverge from a so-called virtual proton source point. When the beam penetrates the patient body up to the position where beam detectors 50 may be located, each beam detector 50 may measure time dependent response 55. However, those responses and the associated water equivalent depths that may be observed by each beam detector 50 may be different from each other. This may be due to the fact that the particles detected in each beam detector 50 have followed a different path in the body. For example, if defining lines from each beam detector 50 to the virtual proton source, these lines may cross the entrance surface of the body at different entrance points 30 and hence the distance traveled by the particles from the entrance point 30 to the point 40 where the beam detector 50 may be located, may differ from detector position to detector position. Any one of the obtained water equivalent depth values obtained for each beam detector 50 may be used to determine what beam energy to apply for performing a treatment irradiation of the body. However, some of the water equivalent depths obtained with the array of beam detectors may be more trustworthy than others due to a problem of range mixing as will be discussed below. There is therefore a need for an additional method to evaluate which one of the beam detectors 50 provides for the most trustworthy information.

When charged particle beam detector 50 comprises an array of semiconductor diodes 110 (or an array of other detectors such as ionization chambers), one may use the following procedure in order to deduce which diodes are trustworthy or not because of range mixing. Owing to the interplay of transverse heterogeneity with multiple Coulomb scattering, charge particles, such as protons, may reach a same point with different energy-loss histories, and therefore, different stopping powers. This may known by one of ordinary skill in the art as 'degradations of the Bragg peak' or 'range mixing'. Range mixing may pose a serious problem because it typically leads to a wrong evaluation of the WED. If one uses an array of semiconductor diodes 110, one may hope that at least a few of them will see pure rather than range-mixed charge particles (protons). It may then be useful to identify diodes 110 that may be less affected by range mixing. The following method may allow for identifying such diodes 110 and classify them according to the amount of range mixing observed.

It may be assumed that time dependent responses 55 acquired for each semiconductor diode 110 change only when range mixing occurs. If two distributions (or time dependent responses 55) differ, at least one of their moments may differ. Accordingly, odd and central moments (the skewness sk and kurtosis k) of time dependent responses 55 acquired during a calibration phase and acquired when determining the at least one WED between entrance point 30 and reference point 40 may be compared. As a measure of agreement, statistical probabilities psk and pk may be used. Very small psk and pk values may indicate high range mixing.

Skewness sk has been defined in Eq. 8 and Eq. 9. Kurtosis k may be defined by the two following equations, Eq. 10 for the discrete case, and Eq. 11 for the continuous case:

$$k = \frac{1}{s\sigma^4} \sum_{i_1}^{i_N} v_i(t_i - m)^4 - 3, \quad \text{(Eq. 10)}$$

$$k = \frac{1}{s\sigma^4} \int_{t_1}^{t_N} v(t)(t - m)^4 - 3. \quad \text{(Eq. 11)}$$

As stated above, the index $i_1$ (resp. $i_N$) may be the index of the first (resp. last) reading of time dependent response 55. When time dependent response 55 is continuous, $t_1$ (resp. $t_N$) may be the time of the beginning (resp. end) of its acquisition. Alternatively, $i_1$ may represent the first reading of a pattern 105 of the time dependent response, or in the continuous case, $t_1$ may represent the time of the beginning of the acquisition of a pattern 105. This last definition may be preferably chosen when dealing with the method of the present disclosure for evaluating range mixing.

Figure 11:
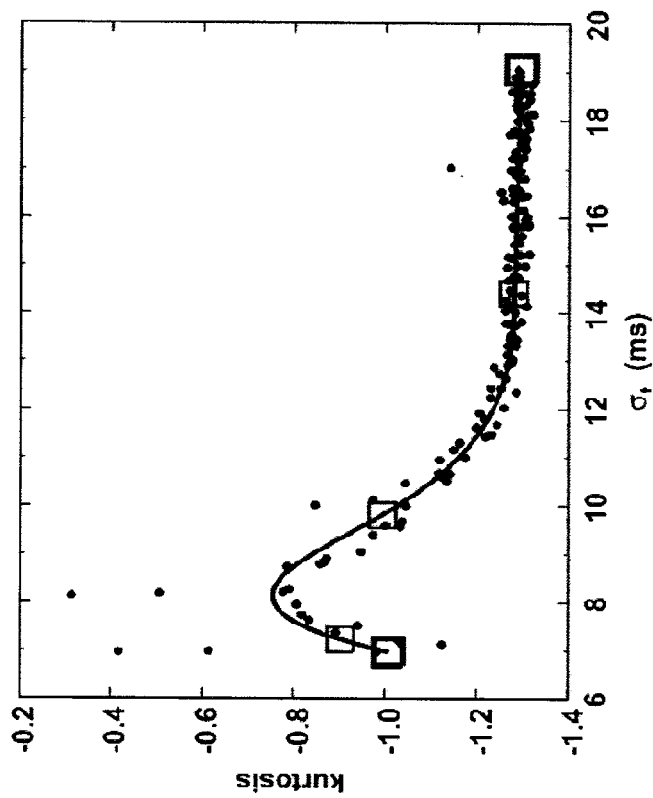
FIG. 11 illustrates an evolution of kurtosis versus root mean square width measured in a homogeneous water phantom, according to an exemplary disclosed embodiment.
Figure 10:
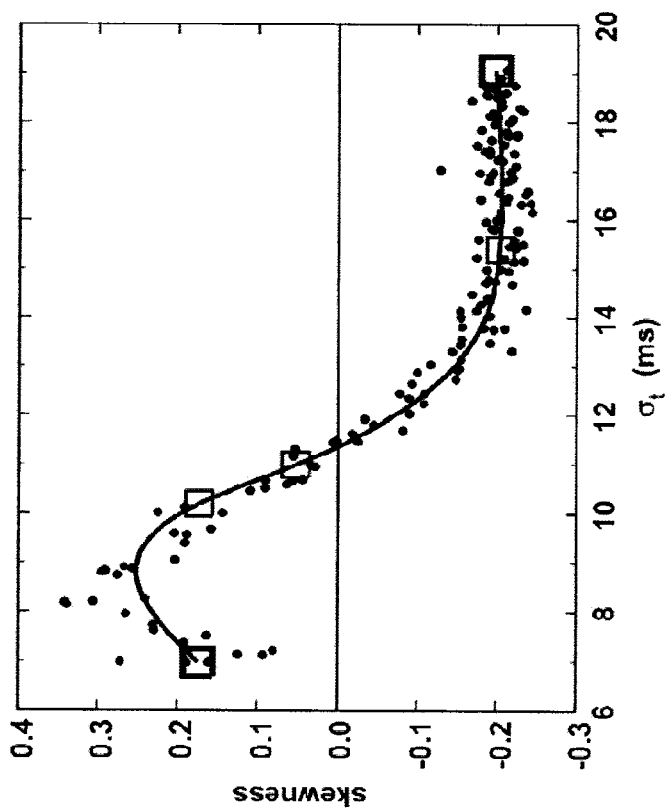
FIG. 10 illustrates an evolution of skewness versus root mean square width measured in a homogeneous water phantom, according to an exemplary disclosed embodiment.

When an array of semiconductor diodes 110 is employed, time dependent response 55 may be acquired for each of them. Each of such time dependent response 55 typically presents patterns 105 when a charged particle beam 10 that is time modulated in energy may be sent to the array comprising the semiconductor diodes 110. Assuming that each time dependent response 55 comprises M patterns 105, the error in mean of sk and k and the deviation of sk and k with respect to natural values $sk_{nat}$ and $k_{nat}$ may be computed for each diode 110 of the array. The values sk, k, $sk_{nat}$ and $k_{nat}$ may represent skewness and kurtosis of patterns 105 measured in a patient (or in a heterogeneous medium) or in a water phantom. The natural values $sk_{nat}$ and $k_{nat}$ may be obtained during a calibration phase during which a semiconductor diode 110, or preferably, the same array of semiconductor diodes 110, is placed in a homogeneous water phantom. During such a calibration phase, functions $sk_{nat}(\sigma)$ and $k_{nat}(\sigma)$ may be determined, where a may be the root mean square width 101 of pattern 105 (and that may be used for determining the WED). A charged particle beam 10 that is time modulated in energy between minimum 70 and maximum 65 energy value may be sent to detector 50 (or to a semiconductor diode 110, or preferably to the array of semiconductor diodes 110) that may be placed at different depths in the homogeneous water phantom. From the time dependent responses 55 acquired during a calibration phase, one may compute $sk_{nat}(\sigma)$ and $k_{nat}(\sigma)$ for semiconductor diode 110 or for each of them if an array of semiconductor diodes 110 is used during the calibration phase. FIGS. 10 and 11 show an exemplary illustration of the evolution of $sk_{nat}(\sigma)$ (and respectively $k_{nat}(\sigma)$) in a homogeneous water phantom. Black dots may represent the measurements, the continuous line may be a cubic spline fit, and the open squares may be the spline points (adjustable parameters of the fit).

Knowing the values of $sk_{nat}(\sigma)$ and $k_{nat}(\sigma)$ in the absence of range mixing (i.e., typically in a homogeneous water phantom), the following procedure may evaluate range mixing in a patient or in a heterogeneous medium. When a charged particle beam 10 that is time modulated in energy is sent to the patient or to a heterogeneous medium, time dependent responses 55 may be acquired for the diodes 110 of an array of semiconductor diodes 110. Assuming that each time dependent response 55 of each diode 110 comprises M patterns 105, the following may be computed:

$$EiM(sk) = \sqrt{2}\,\frac{\langle \sigma_{sk}\rangle_M}{\sqrt{M}}, \quad \text{(Eq. 12)}$$

$$EiM(k) = \sqrt{2}\,\frac{\langle \sigma_k\rangle_M}{\sqrt{M}}, \quad \text{(Eq. 13)}$$

$$psk = 1 - erf\left(\frac{x_{sk}}{\sqrt{2}}\right), \text{ and} \quad \text{(Eq. 14)}$$

$$pk = 1 - erf\left(\frac{x_k}{\sqrt{2}}\right), \quad \text{(Eq. 15)}$$

where:

$$x_{sk} = D_{sk}/EiM(sk) \quad \text{(Eq. 16),}$$

$$x_k = D_k/EiM(k) \quad \text{(Eq. 17),}$$

with:

$$D_{sk} = \frac{sk_{nat} - \langle sk\rangle_M}{sk_{nat}}, \quad \text{(Eq. 18)}$$

$$D_k = \frac{k_{nat} - \langle k\rangle_M}{k_{nat}}. \quad \text{(Eq. 19)}$$

EiM in Eq. 12 (and respectively Eq. 13) may stand for error in mean of sk (and respectively k). $\langle \sigma_{sk}\rangle_M$ (and respectively $\langle \sigma_k\rangle_M$) may represent the mean value over the M patterns 105 of the standard deviations of the skewness sk (respectively kurtosis k) of the different patterns 105 measured in a heterogeneous medium with respect to the natural value, $sk_{nat}$ (and respectively $k_{nat}$), of the skewness of a pattern 105 measured in a water phantom. The comparison between sk and $sk_{nat}$ (or between k and $k_{nat}$) may be carried out for a same root mean square width $\sigma$ 101. The function erf may be known by one of ordinary skilled in the art, and may be given in Eq. 20 as a reminder:

$$erf(z) = \frac{2}{\sqrt{\pi}}\int_0^z e^{-t^2}\,dt. \quad \text{(Eq. 20)}$$

Knowing psk and pk, the product psk*pk may be computed. Depending on its value for each diode 110 of the array of semiconductor diodes 110, some of them may be selected. The higher the product psk*pk is, the least range mixing may be. A diode 110 that may be more trustworthy may be a diode that is subject to less range mixing and so that may present a high value of the product psk*pk. Diodes 110 for which the product psk*pk is higher than 0.5% (and more preferably, higher than 1%) may be selected. The other diodes 110 may not used for evaluating the WED as they may see range-mixed charged particles (or protons). In other words, detectors with a product psk*pk lower than 0.5% may be discarded as they may be subject to much higher gradient of range mixing than any other detectors. Hence, in this way, a range mixing parameter may be defined, which is an indicator of the amount of range mixing observed by the particle beam.

In summary, with this method described for the embodiment where multiple particle detectors may be used, statistical probabilities of skewness and/or kurtosis may be compared with values obtained during a calibration measurement using a water phantom (e.g., homogeneous water phantom), and in a second step, a range mixing parameter may be determined based on observed deviations in probabilities of skewness and/or kurtosis. The obtained range mixing parameter may be an indicator for the amount of range mixing observed by the beam when penetrating the body up to the detector position. During a final step, the various particle detectors (e.g., array of diode detectors) may be classified according to their range mixing parameter. The particle detectors that show the less range mixing may be selected, the information obtained with these specific beam detectors may only be used, and the information obtained with the other beam detectors which show a higher level of range mixing may be discarded.

According to a second aspect of the present disclosure, a device for determining the WED between entrance point 30 and reference point 40 may be used. FIG. 12 illustrates an exemplary embodiment of such a device with other elements. The device of the present disclosure may comprise a unit, such as a computer 200 with a set of subunits or software modules that implement various steps of the method of the present disclosure. Computer 200 may also be an ordinary, single processor personal computer. The different software modules described below may be included in different computers or different units rather than in a single computer 200. Computer 200 may also include an internal memory (not shown) for storing computer program instructions which control how a processing unit within the computer 200 accepts, transforms, and outputs data. The internal memory may include both a volatile and a non-volatile portion. It should be appreciated that the internal memory may be supplemented with computer memory media, such as compact disk, flash memory cards, magnetic disc drives.

Before computer 200 may determine WED of charged particle beam 10 sent to body 20, minimum 70 and maximum 65 energy value may be provided to apparatus 15 (or source setup) by a treatment planning 280. More precisely, these energy values 70, 65 may be sent to a control system 320 of the source setup. The source setup (or apparatus 15) may be able to send a charged particle beam 10 that is time modulated in energy between these minimum 70 and maximum 65 energy values along a beam trajectory 5. A charged particle beam 10 with the maximum (and respectively minimum) energy values 65, 70 may penetrate the body 20 along beam direction 5 until depth 45 that is equal or larger (respectively smaller) than reference distance 35. The depth 45 until which a charged particle beam 10 of a given energy penetrates has been discussed above with FIG. 2.

The device may also comprise charged particle beam detector 50 that may be placed at reference point 40. When charged particle beam detector 50 may be subjected to a charged particle beam 10 that is time modulated in energy between minimum 70 and maximum 65 energy values, it may present a time dependent response 55. This time dependent response 55 can be measured by suitable electronic components. If an ionization chamber is used for the charged particle beam detector 50, a scanning system, for example, that samples, in time, the ionization current generated in an ionization chamber may be used. Control system 230 may acquire time dependent response 55 of charged particle beam detector 50.

From this time dependent response 55, a subunit 240 of computer 200 may determine a value of statistical parameter 100, for instance, the skewness that is given by Eq. 8 for a discrete signal and by Eq. 9 when the signal is continuous. Statistical parameter 100 may be a root mean square width 101 given by Eq. 6 or Eq. 7. Computer 200 may comprise a library of calibration curves 95 obtained for various beam modulations, i.e., for various values of minimum 75 and maximum 65 energies. As discussed above, each of these calibration curves 95 may express a relationship between values of statistical parameter 100 and WEDs. A subunit 250 selects a calibration curve 95 from the library that may be in correspondence with the minimum and maximum energy values. Subunit 260 of computer 200 may eventually determine from this selected calibration curve 95 the WED corresponding to statistical parameter 100 of time dependent response 55. This result may be sent to and displayed on a screen 270.

In one embodiment, charged particle beam detector 50 may comprise semiconductor diode 110. In another embodiment, such a semiconductor diode 110 may be connected to the input of transimpedance amplifier 120 instead of using a usual current integrator. Time dependent response 55 may then be measured at the output of transimpedance amplifier 120. In another embodiment, such a transimpedance amplifier 120 has three stages (FIG. 9): first transimpedance amplifier 125, an inverting voltage amplifier with a gain ranging between 35 and 45, and an output stage whose gain is set to obtain a total gain ranging between 0.4 V/nA and 0.6 V/nA. In yet another embodiment, the first stage (first transimpedance amplifier 125) may have an output of 1 mV/nA and a response time of 5 µs, the second stage (inverting voltage amplifier) may have a gain of 40, and the output stage may be set for a total gain of 0.5 V/nA. Charged particle beam detector 50 may comprise an array of semiconductor diodes 110 placed transversally with respect to charged particle beam 10.

In another aspect of the present disclosure, computer 200 may be configured to determine a water equivalent depth between entrance point 30 and reference point 40, wherein entrance point 30 may lie on an external surface of body 20, and reference point 40 may be a point at which charged particle beam detector 50 is placed. Computer 200 may comprise:
- a software module 230 for acquiring a time dependent response 55 of said charged particle beam detector 50;
- a software module 240 for determining a value of statistical parameter 100 of said time dependent response 55;
- a software module 250 for loading a pre-determined calibration curve 95 expressing a relationship between values of said statistical parameter 100 and WED; and
- a software module 260 for determining from said calibration curve 95 the WED corresponding to the value of the statistical parameter 100 of the time dependent response 55 of the charged particle beam detector 50 placed at the reference point 40.

The following results may be obtained with the method of the present disclosure. With reference to FIGS. 7 and 8, two examples of calibration curve 95 are provided. A proton beam 10 that is modulated in energy may be sent to a water tank. The time dependent response 55 of a PTW Model T60012 diode that is subjected to such a charged particle beam 10 and that is positioned at different depths in a water tank may be recorded during ten modulator cycles 85. At each depth and for each modulator cycles 85, the value of a statistical parameter 100 may be determined. In FIG. 7, the statistical parameter is the skewness given by Eq. 8, whereas FIG. 8 corresponds to the case where the statistical parameter is a root mean square width 101 given by Eq. 6. Then, an averaged value of these two statistical parameters 100 (denoted by $\langle sk \rangle_{10}$ in FIG. 7 and by $\langle \sigma_t \rangle_{10}$ in FIG. 8) may be calculated for each depth by taking the average of the values of the corresponding statistical parameters 100 determined for each modulator cycle 85. The circles in FIGS. 7 and 8 show the averaged values of these statistical parameters 100 at different depths. In FIG. 8, the continuous curve may be a fit corresponding to a cubic polynomial. FIG. 8 shows the smooth and monotonic dependence of the root mean square width 100 with depth (or WED).

Figure 13:
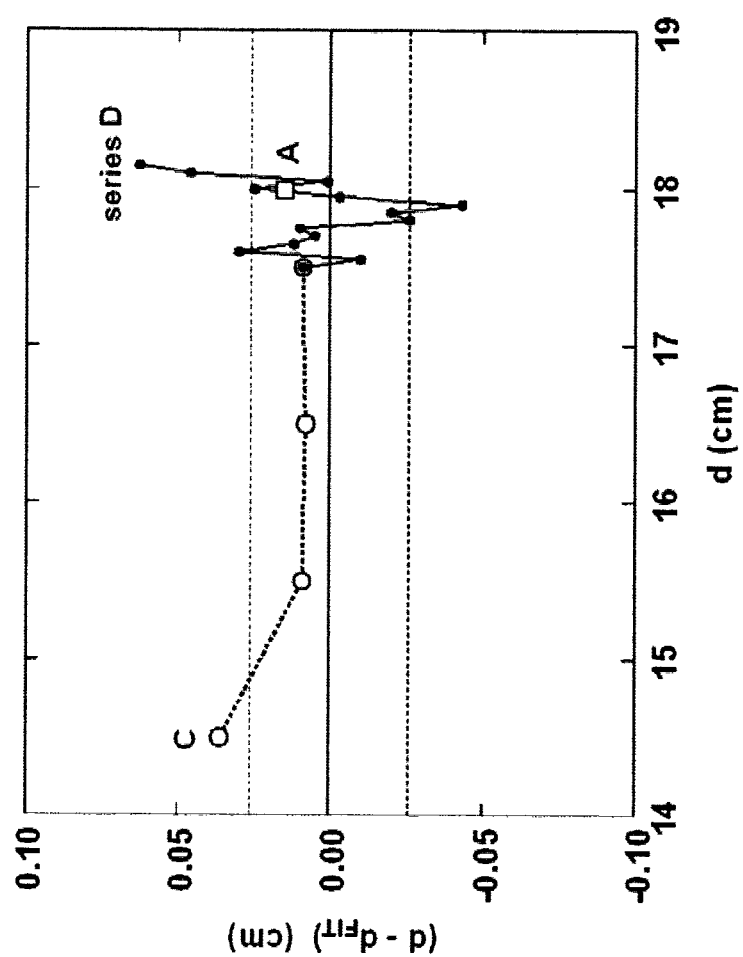
FIG. 13 illustrates, for various depths of a charged particle beam detector in a water tank, the difference between its actual depth and an estimated depth, according to an exemplary disclosed embodiment.

To obtain the experimental calibration curves 95 of FIGS. 7 and 8, a PTW Model T60012 diode connected to a transimpedance amplifier 120 may be employed (FIG. 9). Using the same charged particle beam detector 50 connected to the same transimpedance amplifier 120, three series of measurements A, C, and D may be carried out in a water tank. At the beginning of each series, charged particle beam detector 50 may be driven to 19 cm and subsequently may be moved upstream to avoid backlash, if any. For each series, charged particle beam detector 50 may be subjected at different known depths to an energy modulated proton beam 10, and its time dependence response 55 may be measured and recorded during ten modulator cycles. For each depth and each modulator cycle, the value of a root mean square width 101 may be determined by using equations Eq. 2, Eq. 4, and Eq. 6. Then, for each depth, an averaged value of root mean square width 101 may be determined by taking the average of the individual values of root mean square widths 101 corresponding to the ten modulator cycles. By using the calibration curve of FIG. 8, the corresponding WEDs or depths in the water tank may be determined. Series A may correspond to a preliminary exploration (one point of measurement), series C may correspond to different positions of charged particle beam detector 50 separated by 1 cm steps, and series D may relate to measurements in 0.5 mm steps. FIG. 13 compares the differences between the actual depth of charged particle beam detector 50 and the depth estimated from the measured time dependence responses 55 of charged particle beam detector 50 by using the method of the present disclosure, wherein the open squares correspond to series A, the open circles correspond to series C, and the filled circles correspond to series D. The root mean square scatter of these nineteen points about zero may be 0.026 cm (dashed lines in FIG. 13). Such a value may represent the precision of the method of the present disclosure that is better than the 1 mm of the Lu publication. With more than ten patterns for determining the value of the root mean square width 101 corresponding to each depth in the water tank, the precision of the method of the present disclosure may be increased.

By using the method of the present disclosure, the particle range in-vivo may be verified, and possibly, the parameters of a treatment planning after such a determination of the WED may be modified.

In summary, the present disclosure may include a method for determining the WED between entrance point 30 and reference point 40. The method may comprise the following steps: sending to charged particle beam detector 50 placed at reference point 40 within or beyond body 20 charged particle beam 10 whose energy may be modulated between minimum 70 and maximum 65 energy values; acquiring time dependent response 55 of charged particle beam detector 50; determining from time dependent response 55 a value of statistical parameter 100; providing calibration curve 95; expressing a relationship between values of statistical parameter 100 and WEDs; and extracting from this calibration curve 95 the WED corresponding to the value of statistical parameter 100 determined from time dependent response 55 of charged particle beam detector 50 placed at reference point 40.

The present disclosure may provide additional advantages. For example, a value of a statistical parameter may be easily computed for either smooth or micro pulses (i.e., non-smooth) distributions. Such non-smooth distributions may be typically obtained when the size of the charged particle beam detector is small, for example, when the size is equal or less than around 1 mm$^2$×2.5 μm (2.5 μm being the thickness of the charged particle beam detector along a beam direction of the charged particle beam). As a consequence, the use of a statistical parameter of the time dependent response of a charged particle beam detector may present improved results than a shape matching method that uses, for example, Eq. 1 discussed above in the Lu publication, for determining WED. Moreover, the methods of the present disclosure may be less sensitive to noise. In addition, charged particle beam detector 50 may comprise an array of beam detectors 50 (e.g., semiconductor diodes 110). In this case, the method of the present disclosure may determine statistical probabilities of skewness and kurtosis of each time dependent response 55 acquired for each semiconductor diode 110. Depending on the product value of these statistic probabilities, one or more than one semiconductor diode 110 may be selected as being more trustworthy, which means as being less subject to range mixing.

Any aspect set forth in any embodiment may be used with any other embodiment set forth herein. The present disclosure may reside in each and every novel characteristic feature and each and every combination of characteristic features.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A computer-implemented method for determining a water equivalent depth, between an entrance point and a reference point, of a charged particle beam sent towards a body, wherein said entrance point lies on an external surface of the body, and wherein said reference point corresponds to a location of a charged particle beam detector, the method comprising:
   providing a beam output apparatus for delivering a charged particle beam to said body in a beam direction defined from said entrance point to said reference point;
   choosing a maximum energy value such that a charged particle beam, sent by the beam output apparatus and having said maximum energy value and being sent in said beam direction, would penetrate the body from said entrance point up to at least said reference point;
   choosing a minimum energy value such that a charged particle beam, sent by the beam output apparatus and having said minimum energy value and being sent in said beam direction, would penetrate the body from said entrance point and would be stopped in said body before reaching said reference point;
   sending in said beam direction, from said beam output apparatus, a charged particle beam that is time modulated in energy between said minimum energy value and said maximum energy value;
   acquiring, in response to the sent charged particle beam, a time-dependent response of the charged particle beam detector;
   calculating a first statistical value reflecting a statistical moment of said time-dependent response;
   generating, based on a discrete measurement of a plurality of statistical moments of prior time-dependent responses, a pre-determined calibration curve that expresses a continuous range of water equivalent depths as a function of second statistical values based on the discrete measurement of the plurality of statistical moments of the prior time-dependent responses; and
   determining, from said generated pre-determined calibration curve, the water equivalent depth, between the entrance point and the reference point corresponding to the first statistical value, of the charged particle beam output by the beam output apparatus.

2. The method of claim 1, wherein said reference point is positioned inside said body.

3. The method of claim 1, wherein said reference point is positioned outside said body.

4. The method of claim 1, wherein the charged particle beam detector comprises a semiconductor diode for detecting the charged particle beam.

5. The method of claim 4, wherein said semiconductor diode is connected to an input of a transimpedance amplifier, and wherein said time-dependent response is measured at an output of said transimpedance amplifier.

6. The method of claim 5, wherein said transimpedance amplifier includes a first transimpendance amplifier, an inverting voltage amplifier with a gain ranging between 35 and 45, and an output stage having a gain between the input and the output of said transimpedance amplifier ranging between 0.4 V/nA and 0.6 V/nA.

7. The method of claim 1, wherein the pre-determined calibration curve is obtained by:
   (1) positioning said charged particle beam detector at a given position in a water or water-equivalent calibration phantom;
   (2) sending to said charged particle beam detector the charged particle beam that is time modulated in energy between said minimum and said maximum energy value;
   (3) acquiring a time-dependent response of said charged particle beam detector;
   (4) calculating at least one of a root mean square width, a skewness value, or a kurtosis value of said time-dependent response;
   (5) determining a corresponding water equivalent depth of the time-dependent response, said corresponding water equivalent depth being the distance between the entrance point of said charged particle beam in said calibration phantom and said given position;

(6) repeating steps (1) to (5) more than one time; and (7) establishing a calibration curve that expresses the corresponding determined water equivalent depths as a function of the root mean square widths, skewness values, or kurtosis values.

8. The method of claim 1, wherein the charged particle beam detector comprises an array of semiconductor diodes placed transversally with respect to the charged particle beam.

9. A device for determining a water equivalent depth between an entrance point and a reference point of a charged particle beam sent towards a body, wherein said entrance point lies on an external surface of the body, said device comprising:
   a charged particle beam detector that is placed at the reference point;
   a processor configured to acquire a time-dependent response of said charged particle beam detector from a charged particle beam that is time modulated in energy;
   a processor configured to calculate a first statistical value reflecting a statistical moment of said time-dependent response response;
   a processor configured to generate, based on a discrete measurement of a plurality of statistical moments of prior time dependent responses, a pre-determined calibration curve that expresses a continuous range of water equivalent depths as a function of second statistical values based on the discrete measurement of the plurality of statistical moments of the prior time-dependent responses; and
   a processor configured to determine from said generated pre-determined calibration curve the water equivalent depth corresponding to the first statistical value of the time-dependent response of the charged particle beam detector placed at the reference point.

10. The device of claim 9, wherein the charged particle beam detector comprises a semiconductor diode.

11. The device of claim 10, wherein said semiconductor diode is connected to an input of a transimpedance amplifier, and in that said time-dependent response is measured at an output of said transimpedance amplifier.

12. The device of claim 11, wherein the charged particle beam detector comprises an array of semiconductor diodes placed transversally with respect to the charged particle beam.

13. A method for determining a water equivalent depth between a number of entrance points and a number of corresponding reference points, said entrance points being located on an external surface of a body, said corresponding reference points being points where a corresponding charged particle beam detector is placed, the method, for each entrance point and corresponding reference point, comprising:
   providing a beam output apparatus for delivering a charged particle beam to said body in a beam direction defined from an entrance point to the correspond reference point;
   choosing a maximum energy value such that a charged particle beam, sent by the beam output apparatus and having said maximum energy value and being sent in said beam direction, would penetrate the body from said entrance point up to at least said reference point;
   choosing a minimum energy value such that a charged particle beam, sent by the beam output apparatus and having said minimum energy value and being sent in said beam direction, would penetrate the body from said entrance point and would be stopped in said body before reaching said reference point;
   sending in said beam direction, from said beam output apparatus, a charged particle beam that is time modulated in energy between said minimum energy value and said maximum energy value;
   acquiring a time-dependent response of the charged particle beam detector;
   wherein, for each time-dependent response curve obtained for each of the said corresponding detectors, further comprising the steps of:
      calculating a corresponding statistical value reflecting a statistical moment of the time-dependent response;
      generating, based on a discrete measurement of a plurality of statistical moments of prior time-dependent responses, a pre-determined calibration curve that expresses a continuous range of water equivalent depths as a function of second statistical values based on the discrete measurement of the statistical moments of the plurality of prior time-dependent responses; and
      determining from said generated pre-determined calibration curve the water equivalent depth between the entrance point and the reference point corresponding to the corresponding statistical value.

14. The method of claim 13, further comprising, for each time-dependent response acquired for each of the corresponding charged particle beam detectors, the steps of:
   determining statistical probabilities of skewness and/or kurtosis with respect to the time-dependent response curve;
   comparing statistical probabilities of skewness and/or kurtosis obtained in the previous step with values obtained during a calibration measurement using a water phantom;
   computing a range mixing parameter which is an indicator of deviations in the compared statistical probabilities of skewness and/or kurtosis; and
   classifying the beam detectors according to the range mixing parameter.

15. A method for determining range mixing when a water equivalent depth between a number of entrance points and a number of corresponding reference points is being measured using a charged particle beam, said entrance points being located on an external surface of a body, said corresponding reference points being points where a corresponding charged particle beam detector is placed, the method, for each entrance point and corresponding reference point, comprising:
   providing an apparatus for delivering a charged particle beam to said body in a beam direction defined from an entrance point to the correspond reference point;
   choosing a maximum energy value such that a charged particle beam having said maximum energy value and being sent in said beam direction penetrates the body from said entrance point up to at least said reference point;
   choosing a minimum energy value such that a charged particle beam having said minimum energy value and being sent in said beam direction penetrates the body from said entrance point and is stopped in said body before reaching said reference point;
   sending in said beam direction a charged particle beam that is time modulated in energy between said minimum energy value and said maximum energy value;

acquiring a time-dependent response of the charged particle beam detector;

wherein, for each time-dependent response curve obtained for each of the said corresponding detectors, further comprising the steps of:

determining a first statistical value based on a first statistical moment with respect to the time-dependent response curve;

comparing the first statistical moment obtained in the previous step with a pre-determined calibration curve that expresses a continuous range of water equivalent depths as a function of second statistical values based on a discrete measurement of statistical moments of a plurality of prior time-dependent responses;

computing a range mixing parameter which is an indicator of the observed deviations in the first statistical moment; and classifying the beam detectors according to the range mixing parameter.

16. The device of claim 9, further comprising:
a processor configured to determine statistical probabilities of skewness and/or kurtosis for said time-dependent response; and
a processor configured to compute a range mixing parameter which is an indicator of observed deviations in said statistical probabilities of at least one of skewness or kurtosis when compared with values obtained during a calibration measurement using a water phantom.

17. A device configured to determine a water equivalent depth between an entrance point and a reference point, said entrance point lying on an external surface of a body, said reference point being a point at which a charged particle beam detector is placed, the device comprising:
a processor configured to acquire a time-dependent response of said charged particle beam detector from a charged particle beam that is time modulated in energy;
a processor configured to calculate a first statistical value reflecting a statistical moment of said time-dependent response;
a processor configured to generate, based on a discrete measurement of a plurality of statistical moments of prior time-dependent responses, a pre-determined calibration curve that expresses a continuous range of water equivalent depths as a function of second statistical values based on the discrete measure of the plurality of statistical moments of the prior time-dependent responses; and
a processor configured to determine from said generated pre-determined calibration curve the water equivalent depth corresponding to the first statistical value of the time-dependent response of the charged particle beam detector placed at the reference point.

18. The method of claim 1, further comprising:
controlling the beam output apparatus based on the determined water equivalent depth.

19. The method of claim 1, wherein the first statistical value is one of a root mean square width, a skewness value, or a kurtosis value.

20. The device of claim 9, wherein the first statistical value is one of a root mean square width, a skewness value, or a kurtosis value.

21. The method of claim 13, wherein the first statistical value is one of a root mean square width, a skewness value, or a kurtosis value.

22. The device of claim 17, wherein the first statistical value is one of a root mean square width, a skewness value, or a kurtosis value.

23. The method of claim 1, wherein generating a pre-determined calibration curve comprises:
acquiring a plurality of time-dependent responses of the charged particle beam detector at a respective plurality of known depths;
calculating the second statistical values for each of the plurality of time-dependent responses; and
interpolating a plot of the second statistical values as a function of the respective plurality of known depths.

24. The method of claim 1, wherein the first statistical value is solely a function of said time-dependent response.

* * * * *